United States Patent [19]

King et al.

[11] Patent Number: 5,214,213

[45] Date of Patent: *May 25, 1993

[54] SELECTIVE PRODUCTION OF LINEAR TETRAETHYLENEPENTAMINE AND HYDROXYETHYLDIETHYLENETRIAMINE

[75] Inventors: Stephen W. King, Scott Depot; Lloyd M. Burgess, South Charleston; Arthur R. Doumaux, Jr., Charleston, all of W. Va.

[73] Assignee: Union Carbide Chemicals & Plastics Technology Corporation, Danbury, Conn.

[*] Notice: The portion of the term of this patent subsequent to Jan. 8, 2008 has been disclaimed.

[21] Appl. No.: 501,903

[22] Filed: Mar. 30, 1990

[51] Int. Cl.$^5$ ............... C07C 209/01; C07C 211/02; C07C 209/16; C07D 403/14

[52] U.S. Cl. ........................... 564/480; 502/308; 502/309; 544/358; 544/359; 544/360; 544/401; 544/402; 544/410; 564/470; 564/479; 564/505; 564/506; 564/507; 564/508; 564/511; 564/512

[58] Field of Search ............... 564/479, 470, 480, 505, 564/506, 507, 508, 511, 512; 544/401, 402, 358, 360; 502/308, 309

[56] References Cited

U.S. PATENT DOCUMENTS

| | | | |
|---|---|---|---|
| 1,799,722 | 4/1931 | Arnold | 564/479 |
| 2,073,671 | 4/1931 | Andrews | 260/127 |
| 2,389,500 | 11/1945 | Goshorn | 564/480 |
| 2,467,205 | 4/1949 | Gresham et al. | 260/268 |
| 3,092,457 | 6/1963 | Sprague | 502/309 |
| 3,207,808 | 9/1965 | Bajars | 502/309 |
| 3,734,963 | 5/1973 | Langen, Jr. et al. | 260/563 R |
| 4,036,881 | 7/1977 | Brennan et al. | 564/479 |
| 4,044,053 | 8/1977 | Brennan et al. | 260/583 P |
| 4,314,083 | 2/1982 | Ford et al. | 564/479 |
| 4,316,840 | 2/1982 | Ford et al. | 260/239 BC |
| 4,316,841 | 2/1982 | Ford et al. | 260/239 BC |
| 4,324,917 | 4/1982 | McConnell | 564/479 |
| 4,362,886 | 12/1982 | Ford et al. | 564/479 |
| 4,394,524 | 7/1983 | Ford et al. | 564/479 |
| 4,399,308 | 8/1983 | Ford et al. | 564/479 |
| 4,448,997 | 5/1984 | Brennan | 564/479 |
| 4,463,193 | 7/1984 | Johnson et al. | 564/479 |
| 4,503,253 | 3/1985 | Ford et al. | 564/479 |
| 4,521,600 | 6/1985 | Wells et al. | 544/352 |
| 4,524,143 | 6/1985 | Vanderpool | 502/208 |

(List continued on next page.)

FOREIGN PATENT DOCUMENTS

| | | | |
|---|---|---|---|
| 0290960 | 11/1988 | European Pat. Off. . | |
| 0315189 | 5/1989 | European Pat. Off. . | |
| 0328101 | 8/1989 | European Pat. Off. . | |
| 0331396 | 9/1989 | European Pat. Off. . | |
| 48-96475 | 12/1973 | Japan . | |
| 0171441 | 10/1982 | Japan | 502/309 |
| 78945 | 5/1985 | Japan . | |
| 236752 | 10/1986 | Japan . | |
| 236753 | 10/1986 | Japan . | |
| 307846 | 12/1988 | Japan . | |
| 132550 | 5/1989 | Japan . | |
| 153659 | 6/1989 | Japan . | |
| 157936 | 6/1989 | Japan . | |
| 163159 | 6/1989 | Japan . | |
| 168647 | 7/1989 | Japan . | |
| WO9003963 | 4/1990 | PCT Int'l Appl. | 295/12 |

*Primary Examiner*—Richard L. Raymond
*Assistant Examiner*—Peter G. O'Sullivan
*Attorney, Agent, or Firm*—R. M. Allen

[57] ABSTRACT

This invention relates to a process for making amines having a high yield weight percent of linear tetraethylenepentamine (L-TEPA) and hydroxyethyldiethylenetriamine (HEDETA) by condensing an amino compound in the presence of a condensation catalyst selected from a Group IVB metal oxide, a Group VIB metal-containing substance and a promoted condensation catalyst. This invention also relates to an alkyleneamines producers composition rich in L-TEPA and HEDETA.

18 Claims, No Drawings

U.S. PATENT DOCUMENTS

| | | | |
|---|---|---|---|
| 4,540,822 | 9/1985 | Vanderpool | 564/479 |
| 4,547,591 | 10/1985 | Brennan et al. | 564/479 |
| 4,550,209 | 10/1985 | Unvert et al. | 564/479 |
| 4,552,961 | 11/1985 | Herdle | 544/402 |
| 4,555,582 | 11/1985 | Vanderpool | 564/479 |
| 4,560,798 | 12/1985 | Ford et al. | 564/503 |
| 4,578,517 | 3/1986 | Johnson et al. | 564/479 |
| 4,578,518 | 3/1986 | Vanderpool et al. | 564/479 |
| 4,578,519 | 3/1986 | Larken et al. | 564/479 |
| 4,584,405 | 4/1986 | Vanderpool | 564/479 |
| 4,584,406 | 4/1986 | Vanderpool et al. | 564/479 |
| 4,588,842 | 5/1986 | Vanderpool | 564/479 |
| 4,605,770 | 8/1986 | Ford et al. | 564/479 |
| 4,609,761 | 9/1986 | Watts, Jr. et al. | 564/479 |
| 4,612,397 | 9/1986 | Renken | 564/479 |
| 4,617,418 | 10/1986 | Ford et al. | 564/479 |
| 4,625,030 | 11/1986 | Best | 544/358 |
| 4,683,335 | 7/1987 | Knifton et al. | 564/480 |
| 4,698,427 | 10/1987 | Vanderpool | 544/404 |
| 4,720,588 | 1/1988 | Turcotte et al. | 564/479 |
| 4,806,517 | 2/1989 | Vanderpool et al. | 502/208 |
| 4,822,925 | 4/1989 | Briggs et al. | 568/853 |
| 4,922,024 | 5/1990 | Bowman et al. | 564/480 |
| 4,973,692 | 11/1990 | Burgess et al. | 544/398 |
| 4,983,736 | 1/1991 | Doumaux, Jr. et al. | 544/402 |
| 4,996,363 | 2/1991 | Bowman et al. | 564/470 |
| 5,030,740 | 7/1991 | Bowman et al. | 544/357 |

SELECTIVE PRODUCTION OF LINEAR TETRAETHYLENEPENTAMINE AND HYDROXYETHYLDIETHYLENETRIAMINE

RELATED APPLICATIONS

The following are related, commonly assigned applications, filed on an even date herewith; U.S. patent application Ser. No. 501,917. U.S. patent application Ser. No. 501,919; U.S. patent application Ser. No. 501,906; U.S. patent application Ser. No. 501,907; U.S. patent application Ser. No. 501,998; U.S. patent application Ser. No. 501,826; and U.S. patent application Ser. No. 501,920; all incorporated herein by reference. 07/390,714, The following are related, commonly assigned applications: U.S. patent application Ser. No. 07/136,615, filed Dec. 22, 1987; U.S. patent application Ser. No. 07/390,829, filed Aug. 8, 1989; U.S. patent application Ser. No. 07/390,706, filed Aug. 8, 1989; U.S. patent application Ser. No. 07/390,709, filed Aug. 8, 1989 (now U.S. Pat. No. 4,983,736); U.S. patent application Ser. No. 07/390,828, filed Aug, 8 1989 (now U.S. Pat. No. 5,101,074); U.S. patent application Ser. No. 07/390,708, filed Aug. 8, 1989 now abandoned in favor of continuation Ser. No. 07/742,731, filed Aug. 16, 1991, which in turn has been abandoned in favor of continuation Ser. No. 934,901, filed Aug. 26, 1992); and U.S. patent application Ser. No. 07/390,714, filed Aug. 8, 1989; all incorporated herein by reference.

BRIEF SUMMARY OF THE INVENTION

1. Technical Field

This invention relates to a process for making amines having a high yield weight percent of linear tetraethylenepentamine (L-TEPA) and hydroxyethyldiethylenetriamine (HEDETA) by condensing an amino compound in the presence of a condensation catalyst selected from a Group IVB metal oxide, a Group VIB metal-containing substance and a promoted condensation catalyst.

This invention also relates to an alkyleneamines producers composition rich in L-TEPA and HEDETA.

2. Background of the Invention

There is a substantial body of literature directed to the use of various acid catalysts to effect intramolecular and intermolecular condensation of amino compounds. U.S. Pat. No. 2,073,671 and U.S. Pat. No. 2,467,205 constitute early prior work on the use of acid condensation catalysts to condense amino compounds. U.S. Pat. No. 2,073,671 discusses, in a general fashion, the catalytic intermolecular condensation of alcohols and amines or ammonia using the same phosphate catalysts later favored by U.S. Pat. No. 2,467,205 for the intramolecular condensation of amines. The two patents are not in harmony over the use of other materials as catalysts. To illustrate this point, U.S. Pat. No. 2,073,671 states:

"Alumina, thoria, blue oxide of tungsten, titania, chromic oxide, blue oxide of molybdenum and zirconia have been mentioned in the literature for use as catalysts in carrying out these reactions but their effectiveness is so low that no practical application has been made of their use."

whereas U.S. Pat. No. 2,467,205 in describing the self-condensation of ethylenediamine (EDA) under vapor phase conditions, to initially produce ethyleneamines, but after recycle, eventually generates piperazine (PIP) through multistep condensation reactions, followed by deamination, recommends "dehydration catalysts" which are thereafter characterized as "silica gel, titania gel, alumina, thoria, boron phosphate, aluminum phosphate, and the like."

U.S. Pat. No 2,073,671 describes the condensation catalyst in the following terms:

"... a heated catalyst or contact mass containing phosphorus and especially one or more of the oxygen acids of phosphorus, their anhydrides, their polymers, and their salts; for example, orthophosphoric acid, metaphosphoric acid, pyrophosphoric acid, phosphorous pentoxide, dimetaphosphoric acid, trimetaphosphoric acid, primary ammonium phosphate, secondary ammonium phosphate, normal ammonium phosphate, ammonium metaphosphate, secondary ammonium pyrophosphate, normal ammonium pyrophosphate, aluminum phosphate, aluminum acid phosphate and mixtures of two or more of such materials."

whereas U.S. Pat. No. 2,467,205 describes one of the preferred catalysts as "basic aluminum phosphate".

U.S. Pat. No. 2,454,404 describes the "catalytic deamination of alkylene polyamines" by reacting DETA vapor over solid catalysts such as activated alumina, bauxite, certain aluminum silicates such as kaolin and oxides of thorium, titanium and zirconium.

U.S. Pat. Nos. 2,073,671 and 2,467,205 demonstrate a common experience in using aluminum phosphate as a condensation catalyst to produce aliphatic amines, and U.S. Pat. Nos. 2,454,404 and 2,467,205 contemplate the other solid catalysts for deamination of amines to make heterocyclic noncyclic amines. In general, the reaction conditions under which deamination to effect cyclization occurs are more severe than those employed for condensation to generate noncyclic molecules, all other factors being comparable.

U.S. Pat. Nos. 4,540,822, 4,584,406 and 4,588,842 depict the use of Group IVB metal oxides as supports for phosphorus catalysts used to effect the condensation of amino compounds with alkanolamines.

U.S. Pat. No. 4,683,335 describes the use of tungstophosphoric acid, molybdophosphoric acid or mixtures deposited on titania as catalysts for the condensation of amines and alkanolamines to make polyalkylenepolyamines.

U.S. Pat. Nos. 4,314,083, 4,316,840, 4,362,886 and 4,394,524 disclose the use of certain metal sulfates as useful catalysts for the condensation of alkanolamine and an amino compound. No distinction is made between the sulfur compounds in respect to catalytic efficacy. Sulfuric acid is as good as any metal sulfate, and all metal sulfates are treated as equivalents. At column 8 of U.S. Pat. No. 4,314,083, it is noted that boron sulfate "gave extremely high selectivity at a low level" of EDA. However, selectivity in general was shown to increase with an increase of EDA relative to monoethanolamine (MEA) in the feed. The only specific metal sulfates disclosed in the patents are antimony sulfate, beryllium sulfate, iron sulfate and aluminum sulfate.

In the typical case of the manufacture of alkyleneamines, mixtures with other alkyleneamines (including a variety of polyalkylenepolyamines and cyclic alkylenepolyamines) are formed. The same holds true when the object of the process is to produce polyalkylenepolyamines whether acyclic or cyclic, in that a variety of amino compounds are also formed. Each of these cyclic and acyclic alkyleneamines can be isolated from the mixture.

The acid catalyzed condensation reaction involving the reaction of an alkanolamine with an amino compound in the presence of an acidic catalyst is believed to proceed through the mechanism of esterifying free surface hydroxyl groups on the acid catalyst with the alkanolamine and/or by protonating the alkanolamine in the presence of the acid catalyst, followed by loss of water and amine condensation of the ester or the hydrated species, as the case may be, to form the alkyleneamine. Illustrative prior art directed primarily to the cyclic polyalkylenepolyamines (heterocyclic polyamines), but not necessarily limited to the aforementioned acid condensation reaction, are: U.S. Pat. Nos. 2,937,176, 2,977,363, 2,977,364, 2,985,658, 3,056,788, 3,231,573, 3,167,555, 3,242,183, 3,297,701, 3,172,891, 3,369,019, 3,342,820, 3,956,329, 4,017,494, 4,092,316, 4,182,864, 4,405,784 and 4,514,567; European Patent Applications 0 069 322, 0 111 928 and 0 158 319; East German Patent No. 206,896; Japanese Patent Publication No. 51-141895; and French Patent No. 1,381,243. The evolution of the art to the use of the acid catalyzed condensation reaction to generate acyclic alkyleneamines, particularly acyclic polyalkylenepolyamines, as the predominant products stemmed from the initial disclosure in U.S. Pat. No. 4,036,881, though earlier patent literature fairly well characterized such as effect without labeling it so, see U.S. Pat. No. 2,467,205, supra. The acid catalysts are phosphorus compounds and the reaction is carried out in the liquid phase. The trend in this catalyst direction was early set as demonstrated by U.S. Pat. Nos. 2,073,671 and 2,467,205, supra. A modification of this route includes the addition of ammonia to the reaction, see, for example, U.S. Pat. No. 4,394,524 and U.S. Pat. No. 4,463,193 for the purpose of converting alkanolamine such as MEA in situ to alkylene amine such as EDA by reaction with ammonia, and the EDA is in situ reacted with MEA according to the process of U.S. Pat. No. 4,036,881 to form alkyleneamines.

A summary of the prior art employing said catalysts for making alkyleneamines is set forth in Table I below:

TABLE I

| CITATION | CATALYST TYPE | REACTANTS |
|---|---|---|
| U.S. Pat. No. 2,467,205 | Silica gel, titania gel, alumina, thoria, aluminum phosphate. Preferred catalyst is basic aluminum phosphate. | Vapor phase condensation of EDA over a fixed bed of the catalyst, multipass process shifts from polyethylenepolyamines with the first few cycles. |
| U.S. Pat. No. 4,036,881 | Phosphorus containing substances selected from the group consisting of acidic metal phosphates, phosphoric acid compounds and their anhydrides, phosphorus acid compounds and their anhydrides, alkyl or aryl phosphate esters, alkyl or aryl phosphite esters, alkyl or aryl substituted phosphorous and phosphoric acids wherein said alkyl groups have from 1 to about 8 carbon atoms and said aryl groups have from 6 to about 20 carbon atoms, alkali metal monosalts of phosphoric acid, the thioanalogs of the foregoing, and mixtures of the above. | Alkanolamine and alkyleneamine in liquid phase reaction. |
| U.S. Pat. No. 4,044,053 | Phosphorus containing substances selected from the group consisting of acidic metal phosphates, phosphoric acid compounds and their anhydrides, phosphorus acid compounds and their anhydrides, alkyl or aryl phosphate esters, alkyl or aryl phosphite esters, alkyl or aryl substituted phosphorous acids and phosphoric acids wherein said alkyl groups have from 1 to about 8 carbon atoms and said aryl groups have from 6 to about 20 carbon atoms, alkali metal monosalts of phosphoric acid and mixtures of the above. | Alkanepolyols and alkyleneamine in liquid phase reaction. |
| U.S. Pat. No. 4,314,083 | Salt of a nitrogen or sulfur containing substance or the corresponding acid. | Alkanolamine and an alkyleneamine in liquid phase reaction. |
| U.S. Pat. No. 4,316,840 | Metal nitrates and sulfates including zirconium sulfate. | Reforming linear polyamines. |
| U.S. Pat. No. 4,316,841 | Phosphate, preferably boron phosphate. | Reforming linear polyamines. |
| U.S. Pat. No. 4,324,917 | Phosphorous-containing cation exchange resin. | Alkanolamine and an alkyleneamine in liquid phase reaction. |
| U.S. Pat. No. 4,362,886 | Arsenic, antimony or bismuth | Alkanolamine and an alkylene- |

TABLE I-continued

| CITATION | CATALYST TYPE | REACTANTS |
|---|---|---|
| | containing compounds. Antimony sulfate specifically disclosed. | amine in liquid phase reaction. |
| U.S. Pat. No. 4,399,308 | Lewis acid halide. | Alkanolamine and an alkyleneamine in liquid phase reaction. |
| U.S. Pat. No. 4,394,524 | Phosphorus-containing substance or salt of a sulfur-containing substance, or the corresponding acid. | Ammonia, alkanolamine and an alkyleneamine in liquid phase reaction. |
| U.S. Pat. No. 4,448,997 | Reacts alumina with phosphoric acid, adds ammonium hydroxide. | EDA with MEA. |
| U.S. Pat. No. 4,463,193 | Group IIIB metal acid phosphate. | Ammonia, alkanolamine and an alkyleneamine. |
| U.S. Pat. No. 4,503,253 | Supported phosphoric acid. | Ammonia, alkanolamine and an alkyleneamine. |
| U.S. Pat. No. 4,521,600 | Select hydrogen phosphates and pyrophosphates. | Alkanolamine and an alkyleneamine. |
| U.S. Pat. No. 4,524,143 | Phosphorus impregnated onto zirconium silicate suport. | Alkanolamine and an alkyleneamine. |
| U.S. Pat. No. 4,540,822 | Phosphorus compound deposited on a Group IVB metal oxide support. | Alkanolamine and an alkyleneamine, regenerates the catalyst with $O_2$-containing gas. |
| U.S. Pat. No. 4,547,591 | Silica-alumina alone or in combination with an acidic phosphorus cocatalyst. | An ethyleneamine and an alkanolamine; ethyleneamines; or ammonia and an alkanolamine. |
| U.S. Pat. No. 4,550,209 | An intercalatively catalytically active tetravalent zirconium polymeric reaction product of an organo phosphonic acid or an ester thereof with a compound of tetravalent zirconium reactive therewith. | EDA and MEA. |
| U.S. Pat. No. 4,552,961 | Phosphorus amide compound. | Alkyleneamine and alkanolamine and/or alkylene glycol. |
| U.S. Pat. No. 4,555,582 | Phosphorus chemically bonded to a zirconium silicate support. | MEA and EDA. |
| U.S. Pat. No. 4,560,798 | Rare earth metal or strontium acid phosphate. | MEA. |
| U.S. Pat. No. 4,578,517 | Group IIIB metal acid phosphate. | Ammonia or p-/s-amine and alkanolamine. |
| U.S. Pat. No. 4,578,518 | Thermally activated, calcined, pelleted titania containing titanium triphosphate. " . . . the titania that was used was . . . anatase." (Col. 9, lines 18-19). | MEA and EDA. |
| U.S. Pat. No. 4,578,519 | Thermally activated, calcined, pelleted titania with chemically bonded phosphorus derived from polyphosphoric acid. | MEA and EDA with optional recycle of DETA. |
| U.S. Pat. No. 4,584,405 | Activated carbon, optionally treated to incorporate phosphorus. Activated carbon may be washed with strong mineral acid to remove impurities followed by water wash. Optional treatment follows. | MEA and EDA. |
| U.S. Pat. No. 4,584,406 | Pelleted Group IVB metal oxide with chemically bonded phosphorus derived from phosphoryl chloride or bromide. | MEA and EDA. |
| U.S. Pat. No. 4,588,842 | Thermally activated pelleted Group IVB metal oxide with chemically bonded phosphorus. | MEA and EDA. |
| U.S. Pat. No. 4,605,770 | Group IIA or IIIB metal acid phosphate. | Alkanolamine and an alkyleneamine "in liquid phase". |
| U.S. Pat. No. 4,609,761 | Thermally activated pelleted titania with chemically bonded phosphorus. | MEA and EDA. |
| U.S. Pat. No. 4,612,397 | Thermally activated pelleted titania with chemically bonded phosphorus. | MEA and EDA. |
| U.S. Pat. No. 4,617,418 | Acid catalysts, mentions "beryllium sulfate". | Ammonia, alkanolamine and an alkyleneamine "under vapor phase conditions". |
| Japanese Patent Application #1983 - 185,871, Publication | Variety of phosphorus and metal phosphates including Group IVB phosphates. | Ammonia, alkanolamine and ethyleneamine, with ammonia/alkanolamine molar ratio greater than 11. |

TABLE I-continued

| CITATION | CATALYST TYPE | REACTANTS |
|---|---|---|
| #1985 - 78,945 | | |
| U.S. Pat. No. 4,683,335 | Tungstophosphoric acid, molybdo-phosphoric acid or mixtures deposited on titania. Examples 2-7 characterize titania surface areas of 51, 60 and 120 m$^2$/gm. | Claims reaction of MEA and EDA, but discloses self-condensation reaction of EDA and DETA. |
| Japanese Patent Application #1985 - 078,391, Publication #1986 -236,752 | Group IVB metal oxide with bonded phosphorus. | Ammonia and MEA. |
| Japanese Patent Application #1985 - 078,392, Publication #1986 -236,753 | Group IVB metal oxide with bonded phosphorus. | Ammonia and MEA. |
| U.S. Pat. No. 4,698,427 | Titania having phosphorus thermally chemically bonded to the surface thereof in the form of phosphate bonds. | Diethanolamine and/or hydroxyethyldiethylene-triamine in EDA. |
| U.S. Pat. No. 4,806,517 | Pelleted Group IVB metal oxide with phosphorus thermally chemically bonded to the surface thereof. | MEA and EDA. |
| European Patent Application 331,396 | Titania and zirconia chemically bonded to phosphorus. | MEA and EDA. |

A summary of additional prior art for making alkyleneamines is set forth in Table II below.

TABLE II

| CITATION | CATALYST TYPE | REACTANTS |
|---|---|---|
| Japanese Patent Application #1987 - 312,182, Publication #1989 - 153,659 | Niobium-containing substance. | Ammonia, alkyleneamine and alkylene glycol. |
| Japanese Patent Application #1987 - 325,274, Publication #1989 - 168,647 | Niobium-containing substance added to water-containing liquid. | Ammonia, alkyleneamine and alkanolamine. |
| Japanese Patent Application #1987 - 321,348, Publication #1989 - 163,159 | Niobium oxide obtained from niobium alkoxide. | Ammonia, alkyleneamine and alkanolamine |
| Japanese Patent Application #1987 - 314,132, Publication #1989 - 157,936 | Niobium pentoxide | Ammonia, alkyleneamine and dialkanolamine. |
| Japanese Patent Application #1987 - 290,652, Publication #1989 - 132,550 | Niobium-containing substance. | Ammonia, alkyleneamine and alkanolamine. |
| Japanese Patent Application #1987 - 142,284, Publication #1989 - 307,846 | Tantalum-containing substance. | Ammonia, alkyleneamine and alkanolamine. |
| European Patent Application 315,189 | Mixed oxide containing niobium oxide. | Ammonia, alkyleneamine and alkanolamine. |
| European Patent Application 328,101 | Niobium-containing substance supported on a carrier. | Ammonia, alkyleneamine and alkanolamine. |
| Japanese Patent Application #1989 - 048,699, Publication #1990 - 006,854 | Titania and zirconia chemically bonded with phosphorus in the form of a hydroxy-containing phosphate group. | MEA and EDA. |
| Japanese Patent Application #1988 - 262,861, Publication #1990 - 002,876 | Niobium oxide and titania, alumina, silica or zirconia. | Ammonia, alkyleneamine and alkanolamine. |

TABLE II-continued

| CITATION | CATALYST TYPE | REACTANTS |
| --- | --- | --- |
| Japanese Patent Application #1988 - 290,106, Publication #1990 - 000,735 | Niobium oxide treated with an acid. | Ammonia, alkyleneamine and alkanolamine. |
| Japanese Patent Application #1988 - 027,489, Publication #1990 - 000,736 | Niobium-containing substance on a carrier. | Ammonia, alkyleneamine and alkanolamine. |
| Japanese Patent Application #1988 - 261,366, Publication #1990 - 000,232 | Three constituent catalyst-copper; one or more elements selected from chromium, manganese, iron and zinc; and a platinum group element. | Alcohol or aldehyde and ammonia, a primary amine or a secondary amine. |
| Japanese Patent Application #1988 - 261,368, Publication #1990 - 000,233 | Four constituent catalyst-copper; one or more elements selected from chromium, manganese, iron, cobalt, nickel and zinc; a platinum group element; and one or more elements selected from lithium, sodium, potassium, rubidium, cesium, magnesium, calcium, strontium and barium. | Alcohol or aldehyde and ammonia, a primary amine or a secondary amine. |
| Japanese Patent Application #1988 - 261,369, Publication #1990 - 000,234 | Four constituent catalyst-copper; one or more elements selected from chromium, manganese, iron, cobalt, nickel and zinc; a platinum group element; and one or more elements selected from aluminum, tungsten and molybdenum. | Alcohol or aldehyde and ammonia, a primary amine or a secondary amine. |

A market demand for L-TEPA and HEDETA has been progressively developing in recent years. It would be desirable to satisfy this developing demand from a cost standpoint by modifying slightly the commercial processes directed to the manufacture of polyalkylene polyamines from suitable starting raw materials to the production of L-TEPA and HEDETA as major products.

It would be desirable to have continuously produced compositions, generated by the reaction of diethanolamine (DEA) and EDA or other suitable starting raw materials over a fixed bed of a condensation catalyst under commercial conditions, that are rich in L-TEPA and HEDETA and that are not disproportionately high in AEP and other cyclics.

The above features are provided by this invention.

SUMMARY OF THE INVENTION

This invention relates in general to a process of making amines having a high yield weight percent of L-TEPA and HEDETA which comprises condensing an amino compound in the presence of a condensation catalyst selected from a Group IVB metal oxide, a Group VIB metal-containing substance and a promoted condensation catalyst. The amino compound used herein preferably comprises an alkyleneamine and a dialkanolamine, in particular, EDA and DEA. The condensation catalysts used herein contain sufficient residual bound hydroxyl groups or other groupings which renders catalyst formation possible by loss of water or its chemical equivalent such as ammonium hydroxide.

More particularly, this invention relates to a process of making amines having a high yield weight percent of L-TEPA and HEDETA by the (i) intramolecular condensation of an amino compound to an amine having a lower molecular weight or (ii) the intermolecular condensation of an amino compound with one or more of another amino compound or a compound containing an alcoholic hydroxyl group using a particularly defined condensation catalyst. The process of this invention primarily involves intermolecular condensation reactions. A preferred process involves the manufacture of L-TEPA and HEDETA by an intermolecular condensation reaction utilizing EDA and DEA as reactants and a Group VIB metal-containing substance or a Group IVB metal oxide as the condensation catalyst.

The invention further relates to a continuously generated alkyleneamines producers composition comprising, based on 100 percent of the weight of the composition and exclusive of any water and/or ammonia and/or feed present, a) greater than about 8.0 weight percent of L-TEPA,
b) greater than about 10.0 weight percent of HEDETA,
c) less than about 30.0 weight percent of AEP,
d) less than about 35.0 weight percent of others,
e) a HEDETA to L-TEPA weight ratio of less than about 10.0, and
f) a L-TEPA+HEDETA to AEP weight ratio of greater than about 2.0.

As used herein, the term "amino compound" embraces ammonia and any compound containing nitrogen to which is bonded an active hydrogen. Also, as used herein, the term "oxide" embraces oxides, hydroxides and/or mixtures thereof. Further, as used herein, the term "others" embraces polyalkylene polyamines, by-products and the like.

For purpose of this invention, the chemical elements are identified in accordance with the Periodic Table of the Elements, CAS version, Handbook of Chemistry and Physics, 67th Ed., 1986–87, inside cover. Also, for purposes of this invention, Group IIIB metal oxides embraces the lanthanides and actinides.

DETAILED DESCRIPTION

L-TEPA and HEDETA are very useful commercial products for a variety of applications including fuel oil additives, corrosion inhibitors, fabric softners, epoxy curing agents and others. There is a developing need for the ability to commercially generate larger production quantities of L-TEPA and HEDETA and that is the direction of this invention. The process of this invention provides for the reaction of DEA and EDA or other suitable starting raw materials to produce in a continuous manner a reaction product mixture, termed herein an "alkyleneamines producers composition", in which L-TEPA and HEDETA are principal products of the reaction.

The process of this invention is distinctive insofar as it achieves the generation of high concentrations of L-TEPA and HEDETA in a manner which can be suitably employed in a commercial process, particularly a continuous process, for the manufacture of alkyleneamines. In particular, the process of this invention allows the production of L-TEPA and HEDETA in relatively high yields without generating large amounts of cyclic alkyleneamine products.

As indicated above, this invention relates to a process of making amines having a high yield weight percent of L-TEPA and HEDETA which comprises condensing an amino compound in the presence of a catalytically effective amount of a condensation catalyst selected from a Group IVB metal oxide, a Group VIB metal-containing substance and a promoted condensation catalyst. The amino compound preferably comprises an alkyleneamine and a dialkanolamine, in particular, EDA and DEA.

As also indicated above, this invention relates to a continuously generated alkyleneamines producers composition comprising, based on 100 percent of the weight of the composition and exclusive of any water and/or ammonia and/or feed present, a) greater than about 8.0 weight percent of L-TEPA, b) greater than about 10.0 weight percent of HEDETA, c) less than about 30.0 weight percent of AEP, d) less than about 35.0 weight percent of others, e) a HEDETA to L-TEPA weight ratio of less than about 10.0, and f) a L-TEPA+HEDETA to AEP weight ratio of greater than about 2.0.

The alkyleneamines producers composition of this invention can be subjected to conventional separations techniques for recovering the individual components of the composition. Such techniques are well known in the art and include, for example, distillation.

This invention contemplates the catalyzed condensation by (i) intramolecular condensation of an amino compound to an amine having a lower molecular weight, and (ii) intermolecular condensation of an amino compound with one or more of another amino compound or a compound containing an alcohol hydroxyl group to an amine having a lower, same or higher molecular weight than the reactants, in the presence of a particularly defined condensation catalyst. The process of this invention primarily involves intermolecular condensation reactions.

A wide variety of condensation catalysts can be used in this invention. Illustrative of suitable condensation catalysts for use in this invention include, for example, Group IVB metal oxides, Group VIB metal-containing substances and promoted condensation catalysts.

The Group IVB metal oxide condensation catalysts are preferred catalysts for use in this invention. Suitable Group IVB metal oxide condensation catalysts are disclosed in U.S. patent application Ser. No. 07/390,829, filed Aug. 8, 1989 and incorporated herein by reference. Illustrative of Group IVB metal oxide condensation catalysts include, for example, titanium oxide and zirconium oxide, preferably titanium dioxide and zirconium dioxide including mixtures thereof.

The Group VIB metal-containing condensation catalysts are also preferred catalysts for use in this invention. Suitable Group VIB metal-containing condensation catalysts are disclosed in the above-cited related U.S. patent application Ser. No. 07/390,708, Aug. 8, 1989 and incorporated herein by reference. Illustrative of Group VIB metal-containing condensation catalysts include, for example, one or more oxides of tungsten, chromium, molybdenum or mixtures thereof.

A variety of promoted condensation catalysts are also desirable for use in this invention. Suitable promoted condensation catalysts are disclosed in U.S. patent application Ser. No. 07/390,714, filed Aug. 8, 1989 and incorporated herein by reference. The condensation catalysts are promoted by a condensation catalyst promoter as described hereinafter. Illustrative of such condensation catalysts include, for example, one or more Group IVB metal oxides and Group VIB metal-containing substances.

The condensation catalyst promoter for use in this invention should be capable of promoting the condensation catalyst. The promoting effect can relate to catalytic activity, product selectivity and/or catalyst stability (mechanical or dimensional strength of the catalyst). Illustrative of condensation catalyst promoters for use in this invention can include, for example, one or more metal oxides, one or more metallic phosphates which may or may not have a cyclic structure, one or more metallic polyphosphates having a condensed structure, one or more Group VIB metal-containing substances and one or more conventional materials such as mineral acids or compounds derived from mineral acids. Mixtures of condensation catalyst promoters may also be employed in this invention. For purposes of this invention, the condensation catalyst promoter should be different from the condensation catalyst; however, the condensaton catalyst promoter and the performance moderator described hereinafter can be the same or different.

This invention also embraces the use of vicinal di(-hetero)alkylene organometalates in the selective preparation of L-TEPA and HEDETA. Suitable vicinal di(-hetero)alkylene organometalates are disclosed in U.S. patent application Ser. No. 07/390,828, filed Aug. 8, 1989 and incorporated herein by reference.

The level of activity of the condensation catalysts of the invention is that level which of itself makes the catalysts at least as active in the condensation of amines as, for example, is phosphoric acid on an equivalent basis. Preferably, the condensation catalysts on a support should have a surface area greater than about 20 $m^2/gm$ to as high as about 260 $m^2/gm$ or greater depending upon which metal oxide described below that is employed. In the case of titanium oxides, the surface area should be greater than about 140 $m^2/gm$ to as high as about 260 $m^2/gm$, more preferably, greater than about 160 $m^2/gm$ to as high as about 260 $m^2/gm$, determined according to the single point $N_2$ method. In the case of zirconia oxides, the surface area should be greater than about 70 $m^2/gm$ to as high as about 150 $m^2/gm$, more preferably, greater than about 90 $m^2/gm$ to as high as about 135 $m^2/gm$, determined according to the single point $N_2$ method. It is appreciated that the performance moderators described below which can be used in association with the condensation catalyst and the condensation catalyst promoters described above can affect the surface area of the condensation catalyst. While surface areas described above may be preferred, for purposes of this invention, the surface area of the condensation catalyst should be sufficient to contribute to product selectivity, catalytic activity and/or mechanical or dimensional strength of the catalyst.

Though the condensation catalyst of the invention provides sufficient activity to effect the condensation reaction, certain combinations of reactants and/or product formation can be benefited by treating the catalyst with a catalyst moderator, hereinafter termed a "performance moderator". Performance moderators are widely used to promote the performance of catalysts in areas of selectivity to certain products and the repression of a catalyst's proclivity to generate a broad range of reaction products. A range of suitable materials may impact the condensation catalysts of this invention in the variety of reaction products. The performance moderator may be any material which impacts the condensation catalyst's selection of reaction products or which changes the proportion of any one or more of the reaction products which the condensation catalyst generates at comparable processing conditions. In addition to contributing to product selectivity, the performance moderator may be any material which contributes to catalytic activity and/or catalyst stability (mechanical or dimensional strength).

Illustrative performance moderators for use in this invention can include, for example, one or more metal oxides, one or more metallic phosphates which may or may not have a cyclic structure, one or more metallic polyphosphates having a condensed structure, one or more Group VIB metal-containing substances and one or more conventional materials such as mineral acids or compounds derived from mineral acids. Mixtures of performance moderators may also be employed in this invention. For purposes of this invention, the performance moderator should be different from the condensation catalyst; however, the performance moderator and the condensation catalyst promoter can be the same or different.

Illustrative of metal oxides which may be utilized as performance moderators in association with the condensation catalyst include, for example, one or more of the following: Group IA metal oxides, Group IIA metal oxides, Group IIIB metal oxides (including lanthanides and actinides), Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides, Group VIA metal oxides and Group IVB metal oxides or mixtures thereof. Certain of these metal oxides may also be used as condensation catalysts in accordance with this invention such as Group IVA and IVB metal oxides. Preferred metal oxides are amphoteric or slightly acidic or slightly basic. Preferred metal oxides which may be utilized in association with the condensation catalyst include, for example, one or more oxides of beryllium, scandium, yttrium, terbium, dysprosium, holmium, erbium, thulium, ytterbium, lutetium, titanium, zirconium, hafnium, vanadium, niobium, tantalum, tungsten, iron, cobalt, zinc, silver, aluminum, gallium, indium, silicon, germanium, tin, lead, arsenic, antimony and bismuth.

Group IVB metal oxides such as titanium dioxide and zirconium dioxide and Group IVA metal oxides such as silica and germania are preferred for use in this invention. For mixed metal oxides in which at least one of the metals is titanium, suitable metals in association with titanium may include, for example, one or more of the following: Group IIIB metals such as scandium, yttrium and lanthanum including the lanthanides, Group VB metals such as niobium and tantalum, Group VIB metals such as chromium, molybdenum and tungsten, Group VIII metals such as iron, cobalt and nickel, Group IIB metals such as zinc and cadmium, Group IIIA metals such as boron, aluminum, gallium and indium, Group IVA metals such as silicon, germanium, tin and lead, Group VA metals such as arsenic, antimony and bismuth, and Group IVB metals such as zirconium and hafnium. For mixed metal oxides in which at least one of the metals is zirconium, suitable metals in association with zirconium may include, for example, one or more of the following: Group IVA metals such as silicon, germanium, tin and lead, Group VB metals such as niobium and tantalum, and Group VIB metals such as chromium, molybdenum and tungsten. Certain of these metal oxides may also be effective as condensation catalysts for use in this invention.

Illustrative of mixed metal oxides which may be used as performance moderators in association with the condensation catalyst include, for example, $TiO_2$—$SiO_2$, $TiO_2$—$Al_2O_3$, $TiO_2$—$CdO$, $TiO_2$—$Bi_2O_3$, $TiO_2$—$Sb_2O_5$, $TiO_2$—$SnO_2$, $TiO_2$—$ZrO_2$, $TiO_2$—$BeO$, $TiO_2$—$MgO$, $TiO_2$—$CaO$, $TiO_2$—$SrO$, $TiO_2$—$ZnO$, $TiO_2$—$Ga_2O_3$, $TiO_2$—$Y_2O_3$, $TiO_2$—$La_2O_3$, $TiO_2$—$MoO_3$, $TiO_2$—$Mn_2O_3$, $TiO_2$—$Fe_2O_3$, $TiO_2$—$Co_3O_4$, $TiO_2$—$WO_3$, $TiO_2$—$V_2O_5$, $TiO_2$—$Cr_2O_3$, $TiO_2$—$ThO_2$, $TiO_2$—$Na_2O$, $TiO_2$—$BaO$, $TiO_2$—$CaO$, $TiO_2$—$HfO_2$, $TiO_2$—$Li_2O$, $TiO_2$—$Nb_2O_5$, $TiO_2$—$Ta_2O_5$, $TiO_2$—$Gd_2O_3$, $TiO_2$—$Lu_2O_3$, $TiO_2$—$Yb_2O_3$, $TiO_2$—$CeO_2$, $TiO_2$—$Sc_2O_3$, $TiO_2$—$PbO$, $TiO_2$—$NiO$, $TiO_2$—$CuO$, $TiO_2$—$CoO$, $TiO_2$—$B_2O_3$, $ZrO_2$—$SiO_2$, $ZrO_2$—$Al_2O_3$, $ZrO_2$—$SnO$, $ZrO_2$—$PbO$, $ZrO_2$—$Nb_2O_5$, $ZrO_2$—$Ta_2O_5$, $ZrO_2$—$Cr_2O_3$, $ZrO_2$—$MoO_3$, $ZrO_2$—$WO_3$, $ZrO_2$—$TiO_2$, $ZrO_2$—$HfO_2$, $TiO_2$—$SiO_2$—$Al_2O_3$, $TiO_2$—$SiO_2$—$ZnO$, $TiO_2$—$SiO_2$—$ZrO_2$, $TiO_2$—$SiO_2$—$CuO$, $TiO_2$—$SiO_2$—$MgO$, $TiO_2$—$SiO_2$—$Fe_2O_3$, $TiO_2$—$SiO_2$—$B_2O_3$, $TiO_2$—$SiO_2$—$WO_3$, $TiO_2$—$SiO_2$—$Na_2O$, $TiO_2$—$SiO_2$—$MgO$, $TiO_2$—$SiO_2$—$La_2O_3$, $TiO_2$—$SiO_2$—$Nb_2O_5$, $TiO_2$—$SiO_2$—$Mn_2O_3$, $TiO_2$—$SiO_2$—$Co_3O_4$, $TiO_2$—$SiO_2$—$NiO$, $TiO_2$—$SiO_2$—$PbO$, $TiO_2$—$SiO_2$—$Bi_2O_3$, $TiO_2$—$Al_2O_3$—$ZnO$, $TiO_2$—$Al_2O_3$—$ZrO_2$, $TiO_2$—$Al_2O_3$—$Fe_2O_3$, $TiO_2$—$Al_2O_3$—$WO_3$, $TiO_2$—$Al_2O_3$—$La_2O_3$, $TiO_2$—$Al_2O_3$—$Co_3O_4$, $ZrO_2$—$SiO_2$—$Al_2O_3$, $ZrO_2$—$SiO_2$—$SnO$, $ZrO_2$—$SiO_2$—$Nb_2O_5$, $ZrO_2$—$SiO_2$—$WO_3$, $ZrO_2$—$SiO_2$—$TiO_2$, $ZrO_2$—$SiO_2$—$MoO_3$, $ZrO_2$—$SiO_2$—$HfO_2$, $ZrO_2$—$SiO_2$—$Ta_2O_5$, $ZrO_2$—$Al_2O_3$—$SiO_2$, $ZrO_2$—$Al_2O_3$—$PbO$, $ZrO_2$—$Al_2O_3$—$Nb_2O_5$, $ZrO_2$—$Al_2O_3$—$WO_3$, $ZrO_2$—$Al_2O_3$—$TiO_2$, $ZrO_2$—$Al_2O_3$—$MoO_3$, $ZrO_2$—$HfO_2$—$Al_2O_3$, $ZrO_2$—$HfO_2$—$TiO_2$, and the like. Other suitable mixed metal oxides embraced within the scope of this invention are disclosed by Tanabe et al., Bulletin of the Chemical Society of Japan, Vol. 47(5), pp. 1064–1066 (1974).

The metal oxides described herein which can be used as performance moderators in association with the condensation catalyst may contribute to product selectivity and/or catalytic activity of the reaction and/or stability of the catalyst. The catalyst structure can comprise from about 0 to about 90 percent or greater by weight of the metal oxide, preferably from about 0 to about 75 percent by weight of the metal oxide, and more preferably from about 0 to about 50 percent by weight of the metal oxide, the remainder being the weight of the condensation catalyst. For mixed metal oxides containing titania, higher concentrations of titania can provide very desirable L-TEPA and HEDETA selectivities. As discussed hereinafter, the condensation catalyst of this invention may also contain support(s), binding agent(s) or other additives to stabilize or otherwise help in the manufacture of the catalyst.

The metallic phosphate and polyphosphate performance moderators may or may not have a cyclic structure and may or may not have a condensed structure. Suitable metallic phosphates having a cyclic structure or an acyclic structure are disclosed in U.S. patent application Ser. No. 07/390,706, filed Aug. 8, 1989 and incorporated herein by reference. Suitable metallic polyphosphates having a condensed structure are disclosed in U.S. patent application Ser. No. 07/390,709 filed Aug. 8, 1989, and incorporated herein by reference (now U.S. Pat. No. 4,983,736). Illustrative of metallic phosphate and polyphosphate performance moderators include, for example, metallic orthophosphates ($PO_4^{-3}$), metallic pyrophosphates ($P_2O_7^{-4}$), metallic polyphosphates (including tripolyphosphates ($P_3O_{10}^{-5}$), tetrapolyphosphates ($P_4O_{13}^{-6}$), pentapolyphosphates ($P_5O_{16}^{-7}$) and higher polyphosphates), metallic metaphosphates (including trimetaphosphates ($P_3O_9^{-3}$), tetrametaphosphates ($P_4O_{12}^{-4}$) and other lower and higher metaphosphates) and metallic ultraphosphates (condensed phosphates containing more $P_2O_5$ than corresponds to the metaphosphate structure). Corresponding metallic metaphosphimates, metallic phosphoramidates and metallic amido- and imidophosphates of the above may also be used as performance moderators in accordance with this invention. Suitable metals which can be incorporated into the metallic phosphate and polyphosphate performance moderators include, for example, Group IA metals, Group IIA metals, Group IIIB metals, Group IVB metals, Group VB metals, Group VIB metals, Group VIIB metals, Group VIII metals, Group IB metals, Group IIB metals, Group IIIA metals, Group IVA metals, Group VA metals, Group VIA metals and mixtures thereof.

Illustrative of metallic orthophosphates which may be utilized in this invention include, for example, $NaH_2PO_4$, $KH_2PO_4$, $RbH_2PO_4$, $LiH_2PO_4$, $CsH_2PO_4$, $MgHPO_4$, $CaHPO_4$, $YPO_4$, $CePO_4$, $LaPO_4$, $ThPO_4$, $MnPO_4$, $FePO_4$, $BPO_4$, $AlPO_4$, $BiPO_4$, $Mg(H_2PO_4)_2$, $Ba(H_2PO_4)_2$, $Mg(NH_4)_2PO_4$, $Ca(H_2PO_4)_2$, $La(H_2PO_4)_3$ and the like. Illustrative of metallic pyrophosphates which maybe utilized in this invention include, for example, $Na_2H_2P_2O_7$, $K_2H_2P_2O_7$, $Ca_2P_2O_7$, $Mg_2P_2O_7$, $KMnP_2O_7$, $AgMnP_2O_7$, $BaMnP_2O_7$, $NaMnP_2O_7$, $KCrP_2O_7$, $NaCrP_2O_7$, $Na_4P_2O_7$, $K_4P_2O_7$, $Na_3HP_2O_7$, $NaH_3P_2O_7$, $SiP_2O_7$, $ZrP_2O_7$, $Na_6Fe_2(P_2O_7)_3$, $Na_8Fe_4(P_2O_7)_5$, $Na_6Cu(P_2O_7)_2$, $Na_{32}Cu_{14}(P_2O_7)_{15}$, $Na_4Cu_{18}(P_2O_7)_5$, $Na(NH_4)_2P_2O_7$, $Ca(NH_4)_2P_2O_7$, $MgH_2P_2O_7$, $Mg(NH_4)_2P_2O_7$) and the like. Illustrative of metallic polyphosphates which may be utilized in this invention include, for example, $NaSr_2P_3O_{10}$, $NaCa_2P_3O_{10}$, $Na_2P_3O_{10}$, $Na_5P_3O_{10}$, $K_5P_3O_{10}$, $Na_3MgP_3O_{10}$, $Na_3CuP_3O_{10}$, $Cu_5(P_3O_{10})_2$, $Na_3ZnP_3O_{10}$, $Na_3CdP_3O_{10}$, $Na_6Pb(P_3O_{10})_2$, $Na_3CoP_3O_{10}$, $K_3CoP_3O_{10}$, $Na_3NiP_3O_{10}$, $K_2(NH_4)_3P_3O_{10}$, $Ca(NH_4)_2P_3O_{10}$, $La(NH_4)_3P_3O_{10}$, $NaMgH_2P_3O_{10}$ and the like. Illustrative of metallic metaphosphates which may be utilized in this invention include, for example, $Na_3P_3O_9$, $K_3P_3O_9$, $Ag_3P_3O_9$, $Na_4P_4O_{12}$, $K_4P_4O_{12}$, $Na_2HP_3O_9$, $Na_4Mg(P_3O_9)_2$, $NaSrP_3O_9$, $NaCaP_3O_9$, $NaBaP_3O_9$, $KBaP_3O_9$, $Ca_3(P_3O_9)_2$, $Ba(P_3O_9)_2$, $Na_2Ni_2(P_3O_9)_2$, $Na_4Ni(P_3O_9)_2$, $Na_4Co(P_3O_9)_2$, $Na_4Cd(P_3O_9)_2$ and the like. Illustrative of metallic ultraphosphates which may be utilized in this invention include, for example, $CaP_4O_{11}$, $Ca_2P_6O_{17}$, $Na_8P_{10}O_{29}$, $Na_6P_8O_{23}$, $Na_2CaP_6O_{17}$, $Na_2P_4O_{11}$, $NaBaP_7O_{18}$, $Na_2P_8O_{21}$, $K_4P_6O_{17}$ and the like. The preferred metallic phosphate and polyphosphate performance moderators for use in this invention include Group IA metal dihydrogen orthophosphates, Group IA metal metaphosphates and Group IA metal dihydrogen pyrophosphates, more preferably $NaH_2PO_4$, $Na_3P_3O_9$, $Na_4P_4O_{12}$ and $Na_2H_2P_2O_7$. Other suitable metallic phosphate and polyphosphate performance moderators which are embraced within the scope of this invention are disclosed by Van Wazer, J. R., Phosphorus and Its Compounds, Vol. 1, Interscience Publishers, Inc., New York (1958).

The metallic phosphate and polyphosphate performance moderators can be prepared by conventional methods known in the art. Sodium is believed to be one of a small group of cations effective for stabilizing six-membered cyclic metaphosphates at their temperatures of fusion (about 625° C.) without decomposition to linear and/or other condensed phosphates including mixtures. The formation of cyclic and acyclic metallic phosphate and polyphosphate structures appears to depend on the cation ionic size, the coordination number of the cation and the ionic or covalent nature of the metal-oxygen bond.

While not wishing to be bound by any particular theory, it is believed that those metallic phosphate and polyphosphate performance moderators and promoters encompassed within the scope of this invention having a cyclic structure and possessing ionic character and/or ion exchange capacity contribute to desired activity and product selectivity when used in appropriate amounts as described hereinbelow. While the reaction mixture may initially include one or more metallic phosphates and/or metallic polyphosphates other than metallic phosphates and polyphosphates having a cyclic structure and possessing ionic character and/or ion exchange capacity, it is believed to be desirable that such metallic phosphates and polyphosphates having a cyclic structure and possessing ionic character and/or ion exchange capacity be formed in situ in order to contribute to desired activity and product selectivity. In such instances, the preparation conditions or reaction conditions should allow for the formation of metallic phosphates and polyphosphates having a cyclic structure and possessing ionic character and/or ion exchange capacity. Mixtures of metallic phosphates and polyphosphates having a cyclic structure and possessing ionic character and/or ion exchange capacity with metallic phosphates and polyphosphates having other than a cyclic structure and other than ionic character and/or ion exchange capacity are believed to contribute to desired activity and product selectivity.

Illustrative of Group VIB metal-containing substances which can be utilized as performance moderators in association with the condensation catalyst are described hereinabove. Such Group VIB metal-containing substances can contribute to product selectivity, catalytic activity and/or catalyst stability (mechanical or dimensional strength of the catalyst). Certain of these Group VIB metal-containing substances may also be effective as condensation catalysts for use in this invention.

Illustrative of conventional materials which can be utilized as performance moderators in association with the condensation catalyst include a mineral acid or a compound derived from a mineral acid. Suitable for use as performance moderators are one or more phosphoric acid or a salt of phosphoric acid, hydrogen fluoride, hydrofluoric acid or a fluoride salt, sulfuric acid or a salt of sulfuric acid, and the like. The performance moderator may also be organic esters of phosphoric acid or a salt of phosphoric acid, hydrogen fluoride organic complexes, hydrofluoric acid organic complexes or a fluoride salt organic complexes, organic esters of sulfuric acid or a salt of sulfuric acid, and the like. Suitable salts of phosphoric acid include sodium dihydrogen phosphate, disodium hydrogen phosphate and the like.

A variety of conventional phosphorus-containing substances may be suitable for use as performance moderators in this invention. The conventional substances should be capable of functioning as a performance moderator. Illustrative of conventional phosphorus-containing substances may include, for example, those disclosed in U.S. Pat. No. 4,036,881, U.S. Pat. No. 4,806,517, U.S. Pat. No. 4,617,418, U.S. Pat. No. 4,720,588, U.S. Pat. No. 4,394,524, U.S. Pat. No. 4,540,822, U.S. Pat. No. 4,588,842, U.S. Pat. No. 4,605,770, U.S. Pat. No. 4,683,335, U.S. Pat. No. 4,316,841, U.S. Pat. No. 4,463,193, U.S. Pat. No. 4,503,253, U.S. Pat. No. 4,560,798 and U.S. Pat. No. 4,578,517.

Suitable conventional phosphorus-containing substances which can be employed as performance moderators in this invention include acidic metal phosphates, phosphoric acid compounds and their anhydrides, phosphorous acid compounds and their anhydrides, alkyl or aryl phosphate esters, alkyl or aryl phosphite esters, alkyl or aryl substituted phosphorous acids and phosphoric acids, alkali metal monosalts of phosphoric acid, the thioanalogs of the foregoing, and mixtures of any of the above.

For purposes of this invention, the phosphorus-containing substances used as promoters and performance moderators herein should only be employed in amounts sufficient so as to not adversely affect HEDETA product selectivity. While not wishing to be bound to any particular theory, it is believed that phosphorus-containing substances are catalytically selective for the reaction of HEDETA and an alkyleneamine such as EDA to higher polyalkylene polyamines. Therefore, the amount of a phosphorus-containing substance used as a promoter or performance moderator herein is considered important to achieving amines products having a high yield weight percent of L-TEPA and HEDETA.

The amount of the performance moderator of the mineral acid type used with the condensation catalyst of the invention is not narrowly critical. Generally, the amount does not exceed 25 weight percent of the weight of the catalyst. As a rule, it is desirable to use at least 0.01 weight percent of the weight of the catalyst. Preferably, the amount of performance moderator will range from about 0.2 to about 10 weight percent of the weight of the catalyst. Most preferably, the amount of performance moderator will range from about 0.5 to about 5 weight percent of the weight of the catalyst.

The amount of performance moderator other than the mineral acid type used with the condensation catalyst is not narrowly critical. Generally, the amount does not exceed 90 weight percent of the weight of the catalyst. The amount of performance moderator can range from about 0 to about 90 or greater weight percent of the weight of the catalyst, preferably from about 0 to about 75 weight percent of the weight of the catalyst, and more preferably from about 0 to about 50 weight percent of the weight of the catalyst. Most preferably, the amount of performance moderator will range from about 0.5 to about 25 weight percent of the weight of the catalyst.

The performance moderator can be provided to the condensation catalyst by conventional procedures known in the art. For example, the performance moderator can be provided to the catalyst by impregnating particles or monolithic structures comprising the catalyst with liquid comprising the performance moderator. This is a well known procedure in the art for incorporating additives to a solid support material. The condensation catalyst of the invention may be utilized as solid powders or as fused, bonded or compressed solid pellets, or larger structures in association with the one or more metal oxides, or as coated, fused, bonded or compressed solid pellets, or larger structures, composited with one or more support materials, in association with one or more metal oxides. These solid structures may be treated with the performance moderator by mixing a liquid body of the performance moderator with the solid structure. For example, the condensation catalyst solids may be slurried in the performance moderator, drained, washed and suctioned to remove excess performance moderator and then dried with heat to remove any volatiles accompanying the performance moderator. The drying temperature chosen will depend on the nature of the volatiles to be removed. Usually, the time/temperature for effecting drying will be below the conditions for effecting dehydration to remove bound water from the metal oxide in association with the condensation catalyst. Normally the drying temperature will be greater than about 120° C. and below about 600° C. depending on the thermal stability of the catalyst or the fusion temperature of the particular phosphate specie used if any. The drying time will generally go down as the drying temperature rises and vice versus, and may extend from 5 seconds to about 24 hours.

Alternatively, the performance moderator can be provided to the condensation catalyst at the time of preparing the catalyst in association with one or more metal oxides. For example, one or more metal oxides may be condensed from their respective hydrolyzable monomers to the desired oxides to form oxide powders which can thereafter be blended and compressed with the catalyst to form pellets and larger structures of the metal oxide-containing condensation catalyst of this invention. The one or more metal oxides which can be used in association with the condensation catalyst in accordance with this invention can be provided from metal salts which can be heated to form the metal oxide. It is appreciated that the performance moderator can be incorporated into the molecular bonding configuration of the metal oxide-containing condensation catalyst by conventional procedures known in the art.

The condensation catalysts in association with one or more metal oxides prior to the optional treatment of the performance moderator may be prepared in a wide variety of ways. For example, one or more metal oxides may be provided as a partial condensate on a support, such as a silica or alpha, beta or gamma alumina, silicon carbide, and the like, and then condensed by heating to effect polymerization to the desired oxide form. The metal oxide(s) may be condensed from hydrolyzable monomers to the desired oxide, indeed, to form an oxide powder which can thereafter be compressed in the presence of a condensation catalyst to form pellets and larger structures of the metal oxide-containing condensation catalyst of the invention. A blend of the powder and condensation catalyst can be made into a shapeable paste which can be extruded and cut into pellets according to conventional procedures. The extrudate may thereafter be fired to cure the condensation catalyst and fix the structure. The cut extrudate may be blended with a support material such as those characterized above, and the blend fired to fuse the metal oxide-containing catalyst to the support.

In a preferred embodiment of this invention, a high surface area silica, germania, titania or zirconia can be slurried with an aqueous solution of ammonium metatungstate or sillicotungstic acid, extruded, and calcined at a temperature of about 400° C.

A preferred catalyst structure comprises a Group VIB and/or IVB metal oxide having a surface area of at least about 140 $m^2$/gm which may or may not be bonded to a support material. The term "support," as used herein and in the claims, means a solid structure which does not adversely affect the catalytic properties of the catalyst and is at least as stable as the catalyst to the reaction medium. The support can function as an amine condensation catalyst independent of the condensation catalyst used herein, although it may have lower catalytic activity to the reaction. The support may act in concert with the catalyst to moderate the reaction. Some supports may contribute to the selectivity of the reaction. The catalyst structure can comprise from about 2 to about 60 percent by weight or greater of the support, more preferably from about 10 to about 50 percent by weight of the support, the remainder being the weight of the metal oxide(s) and condensation catalyst. Included in the weight of the support is the weight of any binding agent such as phosphates, sulfates, silicates, fluorides, and the like, and any other additive provided to stabilize or otherwise help in the manufacture of the catalyst. The support may be particles as large or larger than the catalyst component and "glued" to the condensation catalyst and/or metal oxide by virtue of a binding medium.

The support may constitute a separate phase in the process of extruding the catalytic structure. In this embodiment, the support forming material, preferably as a paste is blended with a paste of the condensation catalyst and one or more metal oxides or a partial condensate thereof. The paste may comprise the oxide forms of the support and the condensation catalyst, each blended with water, and/or binding agents. The extrudate of the blend is passed through a multiorificed die and chopped into pellets of the desired sizes. The particles may be doughnut shaped, spherical, and the like. Then the particles are calcined to dry them and complete any condensation reaction in the support and/or the metal oxide-containing condensation catalyst.

The use of supports for the condensation catalyst provides a number of significant advantages. It has been determined that some of the condensation catalysts are not as stable in the amines reaction media when utilized over an extended period of time. When the reaction is effected as a batch reaction, this matter is not a problem. However, when the reaction is effected with the condensation catalyst as part of a fixed bed in a tubular reactor, the preferred procedure for carrying out the invention, it is desirable to have the catalyst be more stable. When the condensation catalyst is combined with the support, it has greater stability for the reaction medium, and therefore, it is better able to be used in a fixed bed of a continuous reactor. The supported catalysts suffer only minimally from the leaching problems that the catalyst per se may have or the problems that are associated with certain conventional catalysts, such as acidic phosphorus compounds on silica.

The reactants used in the condensation process of the invention may be ammonia or organic compound containing —NH— and any compound possessing an alcoholic hydroxyl group, subject to the following: the intramolecular condensation of an amino compound produces an amine having a lower molecular weight, and the intermolecular condensation of an amino compound with one or more of another amino compound or a compound containing an alcoholic hydroxyl group produces an amine having a lower, same or higher molecular weight than the reactants.

Illustrative of suitable reactants in effecting the overall process of the invention, include by way of example:
Ammonia
MEA—monoethanolamine
DEA—diethanolamine
DiHEED—dihydroxyethylethylenediamine
EDA—ethylenediamine
MeEDA—methylethylenediamine
EtEDA—ethylethylenediamine
AEEA—N-(2-aminoethyl)ethanolamine
HEP—N-(2-hydroxyethyl)piperazine
DETA—diethylenetriamine
HEDETA—hydroxyethyldiethylenetriamine
HETETA—hydroxyethyltriethylenetetramine
HETEPA—hydroxyethyltetraethylenepentamine
AEP—N-(2-aminoethyl)piperazine
PEHA—pentaethylenehexamine
PEHA Isomers
HEHA—hexaethylenepentamine
HEHA Isomers
HEOA—heptaethyleneoctamine
HEOA Isomers
HPA—higher polyalkylene polyamines
HPA Isomers
TETA Isomers (TETA's):
TAEA—trisaminoethylamine
TETA—triethylenetetramine
DPE—dipiperazinoethane
DAEP—diaminoethylpiperazine
    PEEDA—piperazinoethylethylenediamine
TEPA—Isomers (TEPA's):
AETAEA—aminoethyltrisaminoethylamine
TEPA—tetraethylenepentamine
AEDPE—aminoethyldipiperazinoethane
AEDAEP—aminoethyldiaminoethylpiperazine
AEPEEDA—aminoethylpiperazinoethylethylenediamine
iAEPEEDA—isoaminoethylpiperazinoethylethylenediamine
BPEA—bispiperazinoethylamine The foregoing also can represent the products of the reaction. For example, ammonia and MEA are frequently employed to produce EDA along with a variety of other amines, most of which are set forth above. Further, alkylene oxides such as ethylene oxide can be employed with ammonia and a variety of other amines to produce polyalkylene polyamines in accordance with this invention.

Glycol compounds can also be employed in the preparation of amines. Glycol compounds embrace diols and polyols. Illustrative of glycol compounds include alkylene glycols such as ethylene glycol.

The feed space velocity, feed mole ratio and reaction temperature and pressure are not narrowly critical and can vary over a wide range. The selection of these operating variables is dependent on desired conversions and product selectivity.

In particular, when DEA and EDA are employed as reactants in the process of this invention, an increase in DEA space velocity or EDA/DEA feed mole ratio will decrease conversion, while an increase in temperature will increase conversion. Typically, it is desired to operate at a high enough pressure to maintain the reactants primarily in the liquid phase. At a particular DEA space velocity, EDA/DEA feed mole ratio and temperature, the conversation will generally decrease if the pressure is lowered until the flow changes from liquid to vapor.

Lower reaction temperatures generally provide higher selectivity to desired products. As the EDA/DEA feed mole ratio increases, the selectivity to desired products increases. The EDA/DEA feed mole ratio may be used to adjust the relative amounts of L-TEPA and HEDETA. As the EDA/DEA feed mole ratio is increased, the L-TEPA to HEDETA weight ratio increases.

The process may be effected in the liquid or vapor or supercritical liquid states or mixtures thereof though the actual reaction is believed to occur on the catalyst's solid surface in the absorbed state. In this context, the vapor phase reaction is intended to refer to the general vapor state of the reactants. Though the reaction conditions may range from subatmospheric to superatmospheric conditions, it is desirable to run the reaction from about 50 psig to about 3,000 psig, preferably from about 200 psig to about 2,000 psig.

The temperature of the reaction may be as low as about 125° C. to about 400° C. Preferably, the reaction temperature ranges from about 150° C. to about 350° C., and most preferably from about 225° C. to about 325° C.

The reaction may be effected by the incremental addition of one of the reactants to the other or by the joint addition of the reactants to the catalyst. The preferred process effects the reaction in a continuous manner over a fixed bed of the condensation catalyst in a tubular reactor. However, the reaction may be carried out by slurrying the catalyst in the reactants or in a batch mode in an autoclave. An inert such as nitrogen, methane, hydrogen and the like can be used in the reaction process.

The process of the invention provides the ability to selectively generate the manufacture of desirable L-TEPA and HEDETA without generating large amounts of cyclic alkyleneamine products such as AEP and HEP. The alkyleneamines producers composition of this invention has a L-TEPA+HEDETA to AEP weight ratio of greater than about 2.0 and a HEDETA to L-TEPA weight ratio of less than about 10.0.

This invention is further illustrated by certain of the following examples:

EXAMPLES

In the examples set forth in the tables below, the catalyst of choice was placed in a tubular reactor having an outside diameter of 1 inch and an overall length of 30 inches. The catalyst portion of the reactor comprised a length of 24 inches, capable of accommodating 150 cubic centimeters of catalyst. The reactor was made of 316 stainless steel.

For each of the examples, the tubular reaction system was brought to the designated conditions. The DEA and EDA were premixed to the appropriate feed mole ratio and then pressure fed to the system. The liquid feed was then mixed with nitrogen (if used) and this mixture was passed to a preheater prior to entering the reaction zone.

The reaction mixture was passed through the reaction zone in a downflow fashion. The pressure in the reaction zone was controlled by a motor valve at the outlet of the reactor. After leaving the reaction zone, the pressure of the stream was reduced from that of the reaction zone to slightly above atmospheric. This stream was then passed through a trap where the nitrogen (if used) was separated from the condensables which were collected in a semi-batch fashion. The condensable sample, which contains unreacted DEA and EDA and the products of the reaction, was then analyzed for water by a Karl-Fisher procedure and for organics (amines) by capillary gas chromatography.

The catalysts employed are identified as follows:

| Designation | Composition | Physical Properties |
| --- | --- | --- |
| A | $TiO_2$ (anatase)/ $WO_3$ $TiO_2/WO_3$ wt. ratio = 80/20 | Particle size: 1/16 inch cylindrical extrudates. |
| B | $TiO_2$ (anatase)/ $WO_3$ $TiO_2/WO_3$ wt. ratio = 80/20 | Particle size: ⅛ inch cylindrical extrudates; Catalyst surface area: 227.9 $m^2$/gm. |
| C | $TiO_2$ (anatase)/ $WO_3$ $TiO_2/WO_3$ wt. ratio = 80/20 | Particle size: 1/16 inch cylindrical extrudates; Catalyst surface area: 166.3 $m^2$/gm. |

The catalysts and/or supports employed in the examples hereinafter were obtained from Norton Company, Akron, Ohio. Certain of the catalysts and/or supports were subsequently treated as follows:

Catalyst A preparation: Silicotungstic acid (18.0 grams) was dissolved in distilled water (45 milliliters) and an aliquot sufficient to wet the $TiO_2/WO_3$ support (55 grams) was used. After wetting, the catalyst was calcined at a temperature of 350° C. for a period of 1 hour. The impregnation and calcination steps were repeated twice more to give the catalyst.

TABLE I

| Example No. | 1 | 2 | 3 | 4 | 5 | 6 | 7 | 8 | 9 | 10 |
| --- | --- | --- | --- | --- | --- | --- | --- | --- | --- | --- |
| Process Parameters | | | | | | | | | | |
| Catalyst Type | A | A | A | A | A | A | A | A | A | A |
| Catalyst Weight, gm. | 50 | 50 | 50 | 50 | 50 | 50 | 50 | 50 | 50 | 50 |

TABLE I-continued

| Example No. | 1 | 2 | 3 | 4 | 5 | 6 | 7 | 8 | 9 | 10 |
|---|---|---|---|---|---|---|---|---|---|---|
| Temperature, °C. | 269.6 | 280 | 274.4 | 285.3 | 289.8 | 295.5 | 279.5 | 284.7 | 266.3 | 269.9 |
| Pressure, psig | 614.7 | 614.7 | 614.7 | 614.7 | 614.7 | 614.7 | 614.7 | 614.7 | 614.7 | 614.7 |
| Time on Organics, hrs. | 494.5 | 499 | 518.5 | 523 | 543 | 547 | 566.5 | 571 | 589.5 | 614.5 |
| DEA SV, gmol/hr/kgcat | 2.43 | 3.21 | 2.13 | 2.52 | 2.01 | 3.14 | 2.40 | 2.61 | 3.45 | 2.52 |
| EDA/DEA mole ratio | 4.00 | 4.00 | 4.00 | 4.00 | 4.00 | 4.00 | 4.00 | 4.00 | 4.00 | 4.00 |
| Crude Product Composition, wt. % | | | | | | | | | | |
| AEP | 7.14 | 8.45 | 7.18 | 10.42 | 12.71 | 15.75 | 9.03 | 9.46 | 4.93 | 4.82 |
| HEDETA | 61.88 | 58.00 | 64.98 | 52.05 | 41.00 | 31.04 | 58.45 | 54.77 | 74.23 | 75.57 |
| L-TEPA | 11.35 | 13.04 | 11.98 | 15.24 | 16.90 | 18.51 | 12.89 | 14.82 | 8.36 | 8.47 |
| Others | 19.64 | 20.51 | 15.86 | 22.29 | 29.38 | 34.70 | 19.63 | 20.95 | 12.48 | 11.14 |
| Calculated Results | | | | | | | | | | |
| DEA Conversion, % | 41.26 | 51.90 | 47.05 | 60.93 | 74.52 | 83.31 | 56.92 | 63.94 | 38.94 | 35.97 |
| EDA Conversion, % | 5.31 | 8.86 | 9.00 | 12.01 | 12.42 | 13.61 | 10.98 | 12.68 | 5.26 | 5.42 |
| HEDETA/AEP, weight ratio | 8.67 | 6.86 | 9.05 | 5.00 | 3.23 | 1.97 | 6.47 | 5.79 | 15.06 | 15.68 |
| HEDETA + L-TEPA/AEP, weight ratio | 10.25 | 8.41 | 10.72 | 6.46 | 4.56 | 3.15 | 7.90 | 7.36 | 16.75 | 17.44 |
| HEDETA/L-TEPA, weight ratio | 5.45 | 4.45 | 5.42 | 3.41 | 2.43 | 1.68 | 4.53 | 3.70 | 8.88 | 8.93 |

TABLE II

| Example No. | 11 | 12 | 13 | 14 | 15 | 16 | 17 | 18 | 19 | 20 |
|---|---|---|---|---|---|---|---|---|---|---|
| Process Parameters | | | | | | | | | | |
| Catalyst Type | B | B | B | B | B | B | B | B | B | B |
| Catalyst Weight, gm. | 50 | 50 | 50 | 50 | 50 | 50 | 50 | 50 | 50 | 50 |
| Temperature, °C. | 269.6 | 280 | 274.4 | 285.3 | 289.8 | 295.5 | 279.5 | 284.7 | 266.3 | 269.9 |
| Pressure, psig | 614.7 | 614.7 | 614.7 | 614.7 | 614.7 | 614.7 | 614.7 | 614.7 | 614.7 | 614.7 |
| Time on Organics, hrs. | 494.5 | 499 | 518.5 | 523 | 543 | 547 | 566.5 | 571 | 589.5 | 614.5 |
| DEA SV, gmol/hr/kgcat | 2.50 | 3.03 | 2.09 | 2.95 | 2.23 | 3.23 | 2.34 | 3.31 | 2.63 | 2.88 |
| EDA/DEA mole ratio | 4.00 | 4.00 | 4.00 | 4.00 | 4.00 | 4.00 | 4.00 | 4.00 | 4.00 | 4.00 |
| Crude Product Composition, wt. % | | | | | | | | | | |
| AEP | 7.54 | 9.94 | 8.61 | 11.93 | 16.58 | 19.02 | 11.17 | 10.93 | 6.72 | 6.51 |
| HEDETA | 65.92 | 55.04 | 62.84 | 48.07 | 30.07 | 24.99 | 51.26 | 49.51 | 70.52 | 69.95 |
| L-TEPA | 13.06 | 17.02 | 15.29 | 19.72 | 26.42 | 23.89 | 17.97 | 19.10 | 11.83 | 12.30 |
| Others | 13.48 | 18.00 | 13.26 | 20.28 | 26.93 | 32.09 | 19.60 | 20.45 | 10.93 | 11.24 |
| Calculated Results | | | | | | | | | | |
| DEA Conversion, % | 52.87 | 65.35 | 57.72 | 77.11 | 88.18 | 90.86 | 72.97 | 74.15 | 51.51 | 51.96 |
| EDA Conversion, % | 6.46 | 11.91 | 9.85 | 12.31 | 13.89 | 12.68 | 12.81 | 13.78 | 8.48 | 9.03 |
| HEDETA/AEP, weight ratio | 8.75 | 5.54 | 7.30 | 4.03 | 1.81 | 1.31 | 4.59 | 4.53 | 10.50 | 10.75 |
| HEDETA + L-TEPA/AEP, weight ratio | 10.48 | 7.25 | 9.07 | 5.68 | 3.41 | 2.57 | 6.20 | 6.28 | 12.26 | 12.64 |
| HEDETA/L-TEPA, weight ratio | 5.05 | 3.23 | 4.11 | 2.44 | 1.14 | 1.05 | 2.85 | 2.59 | 5.96 | 5.69 |

TABLE III

| Example No. | 21 | 22 | 23 | 24 | 25 | 26 | 27 | 28 | 29 | 30 |
|---|---|---|---|---|---|---|---|---|---|---|
| Process Parameters | | | | | | | | | | |
| Catalyst Type | C | C | C | C | C | C | C | C | C | C |
| Catalyst Weight, gm. | 50 | 50 | 50 | 50 | 50 | 50 | 50 | 50 | 50 | 50 |
| Temperature, °C. | 269.6 | 280 | 274.4 | 285.3 | 289.8 | 295.5 | 279.5 | 284.7 | 266.3 | 269.9 |
| Pressure, psig | 614.7 | 614.7 | 614.7 | 614.7 | 614.7 | 614.7 | 614.7 | 614.7 | 614.7 | 614.7 |
| Time on Organics, hrs. | 494.5 | 499 | 518.5 | 523 | 543 | 547 | 566.5 | 571 | 589.5 | 614.5 |
| DEA SV, gmol/hr/kgcat | 2.40 | 2.94 | 2.04 | 2.79 | 2.27 | 2.69 | 2.22 | 2.57 | 2.35 | 2.76 |
| EDA/DEA mole ratio | 4.00 | 4.00 | 4.00 | 4.00 | 4.00 | 4.00 | 4.00 | 4.00 | 4.00 | 4.00 |
| Crude Product Composition, wt. % | | | | | | | | | | |
| AEP | 6.41 | 8.18 | 7.00 | 10.31 | 12.76 | 16.86 | 8.86 | 9.49 | 5.88 | 5.92 |
| HEDETA | 66.47 | 61.14 | 66.46 | 48.36 | 41.83 | 24.53 | 56.24 | 50.98 | 71.80 | 70.90 |
| L-TEPA | 10.52 | 14.00 | 11.84 | 16.88 | 19.64 | 25.93 | 15.25 | 17.32 | 10.12 | 10.12 |
| Others | 16.60 | 16.68 | 14.71 | 24.46 | 25.76 | 32.67 | 19.65 | 22.22 | 12.20 | 13.06 |

TABLE III-continued

| Example No. | 21 | 22 | 23 | 24 | 25 | 26 | 27 | 28 | 29 | 30 |
|---|---|---|---|---|---|---|---|---|---|---|
| Calculated Results | | | | | | | | | | |
| DEA Conversion, % | 48.84 | 61.29 | 52.42 | 75.05 | 81.22 | 91.80 | 66.48 | 73.49 | 47.55 | 48.25 |
| EDA Conversion, % | 5.53 | 8.38 | 7.40 | 13.04 | 10.65 | 12.39 | 13.32 | 13.88 | 7.79 | 8.27 |
| HEDETA/AEP, weight ratio | 10.37 | 7.48 | 9.50 | 4.69 | 3.28 | 1.45 | 6.35 | 5.37 | 12.22 | 11.98 |
| HEDETA + L-TEPA/AEP, weight ratio | 12.01 | 9.19 | 11.19 | 6.33 | 4.82 | 2.99 | 8.07 | 7.20 | 13.94 | 13.69 |
| HEDETA/L-TEPA, weight ratio | 6.32 | 4.37 | 5.62 | 2.87 | 2.13 | 0.95 | 3.69 | 2.94 | 7.09 | 7.00 |

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A process for making linear tetraethylenepentamine and hydroxyethyldiethylenetriamine comprising condensing, in the absence of hydrogen as a reactant, ethylenediamine and diethanolamine under condensation conditions including the presence of a catalytically effective amount of a condensation catalyst consisting essentially of a metatungstate and one or more Group IVB metal oxides, wherein the ethylenediamine to diethanolamine feed mole ratio is sufficient to provide under condensation conditions an amines product, based on 100 percent of the weight of the amines product and exclusive of any water and/or ammonia and/or feed present,
    (a) greater than about 8.0 weight percent of L-TEPA,
    (b) greater than about 10.0 weight percent of HEDETA,
    (c) less than about 30.0 weight percent of AEP,
    (d) less than about 35.0 weight percent of others,
    (e) a HEDETA to L-TEPA weight ratio of less than about 10.0, and
    (f) a L-TEPA+HEDETA to AEP weight ratio of greater than about 2.0.

2. The process of claim 1 wherein the Group IVB metal oxide comprises a high surface area titanium oxide or zirconium oxide.

3. The process of claim 1 wherein the condensation catalyst has a surface area greater than about 70 cm$^2$/gm.

4. The process of claim 2 wherein the titanium oxide comprises titanium dioxide and the zirconium oxide comprises zirconium dioxide.

5. The process of claim 2 wherein the condensation catalyst has a surface area greater than about 140 m$^2$/gm.

6. The process of claim 2 wherein the condensation catalyst has a surface area greater than about 70 m$^2$/gm.

7. The process of claim 1 wherein the Group IVB metal oxide comprises from about 25 weight percent to about 90 weight percent of the weight of the catalyst.

8. The process of claim 1 wherein the Group IVB metal oxide comprises from about 50 weight percent to about 90 weight percent of the weight of the catalyst.

9. The process of claim 1 wherein the Group IVB metal oxide comprises from about 75 weight percent to about 90 weight percent of the weight of the catalyst.

10. The process of claim 1 wherein the condensation catalyst is associated with a support material.

11. The process of claim 10 wherein the support comprises an alumina material or an alumina-silica material.

12. The process of claim 10 wherein the support comprises a silica material or a silica-alumina material.

13. The process of claim 10 wherein the support comprises from about 2 to about 50 percent by weight of the condensation catalyst.

14. The process of claim 1 wherein the ethylenediamine and diethanolamine are condensed in the presence of ammonia.

15. The process of claim 1 wherein the amines product has a L-TEPA yield weight percent of greater than about 12.0 and an HEDETA yield weight percent of greater than about 20.0, based on 100 percent of the weight of the product and exclusive of any water and/or ammonia and/or feed present.

16. The process of claim 1 which is conducted at a temperature of from about 125° C. to about 400° C.

17. The process of claim 1 which is conducted at a pressure of from about 50 psig to about 3000 psig.

18. The process of claim 1 which is effected in the liquid or vapor or supercritical liquid states.

* * * * *